US00PP07859P

United States Patent [19]

Jessel, Jr.

[11] Patent Number: Plant 7,859

[45] Date of Patent: Apr. 28, 1992

[54] CARNATION PLANT NAMED 'CFPC JUBILEE'

[75] Inventor: Walter H. Jessel, Jr., Salinas, Calif.

[73] Assignee: California Florida Plant Co., L.P., Salinas, Calif.

[21] Appl. No.: 580,251

[22] Filed: Sep. 10, 1990

[51] Int. Cl.[5] ..... A01H 5/00

[52] U.S. Cl. ..... Plt./72

[58] Field of Search ..... Plt./70, 71, 72, 73

[56] References Cited

U.S. PATENT DOCUMENTS

| | | | |
|---|---|---|---|
| P.P. 478 | 7/1941 | Honaker | Plt. 72 |
| P.P. 547 | 10/1942 | Canup | Plt. 72 |
| P.P. 553 | 10/1942 | Klug | Plt. 72 |
| P.P. 805 | 8/1948 | Symonds | Plt. 72 |

*Primary Examiner*—Howard J. Locker

*Attorney, Agent, or Firm*—Christie, Parker & Hale

[57] ABSTRACT

A new and unusual carnation of deep pink coloration.

1 Drawing Sheet

BACKGROUND OF THE INVENTION

Carnation varieties producing flowers of many different colors are well known. However, it is desirable to provide a new standard variety of carnation producing flowers having deep pink coloration that fades smoothly.

SUMMARY OF THE INVENTION

The present invention relates to a new and distinct variety of carnation plant which was originated by me in a controlled breeding program by my crossing as seed parent, the variety known as 'Vanya' (varietal denomination 'Londapo') (U.S. Plant Pat. No. 5,515) and as pollen parent, a numbered but unnamed and unpatented seedling of my creation. The varietal denomination of this new carnation is 'CFPC Jubilee'.

Among the novel characteristics possessed by the new variety which distinguish it from its parents and all other varieties of which I am aware is that it produces high quality, large, unusual deep "fuchsia pink" standard flowers that fade smoothly and do not burn or "blue" the petal edges. Plants of the new variety have very high production and excellent vase-life.

Asexual reproduction by propagation by side shoot cuttings of the new variety as performed in Fremont and Salinas, Calif., shows that the foregoing and other distinguishing characteristics come true to form and are established and transmitted through succeeding propagations.

BRIEF DESCRIPTION OF THE ILLUSTRATION

The accompanying illustration shows a typical specimen of the vegetative growth and flower of the new variety depicted in color as nearly true as it is reasonably possible to make the same in a color illustration of this character.

DESCRIPTION OF THE NEW VARIETY

The new variety, 'CFPC Jubilee', produces large deep pink flowers that fade smoothly and do not burn or blue and are long lasting after cutting. It has been determined that its vase-life is 18 to 21-days. The stems are strong and not brittle. The new variety also has a strong calyx with no splitting having been observed. Therefore, taping or banding is not necessary. 'CFPC Jubilee' has a very high flower production with excellent "come-back". The cut grade of the flowers is mostly "fancy". The characteristics heretofore and hereinafter described, make CFPC Jubilee espcially suitable for commercial cut flower production.

The following is a detailed description of my new variety, with color terminology in accordance with The Royal Horticultural Society Colour Chart (R.H.S.C.C.). The terminology used in the color description herein refers to plate numbers in the aforementioned color chart. Color designations and color descriptions may deviate slightly from the stated values from flowering-to-flowering but the deviations will be within the range expected from varying environmental, seasonal and cultural conditions.

The information provided herein is based on observations of plants grown inside commercial greenhouses at Fremont, Calif. The height of plant and flower and foliage size are established as an average using standard commercial cultural practices.

Name: 'CFPC Jubilee'.

Classification:

*Botanical.*—*Dianthus caryophyllus.*

*Commercial.*—Carnation, standard disbud type.

Parentage:

*Female parent.*—'*Vanya*'.

*Male parent.*—Unnamed seedling (No. 0095).

Plant:

*Growing habit.*—Herbaceous, semi-upright.

*Blooming habit.*—Terminal as a standard.

*Blooming season.*—Year round.

*Rooting time.*—17-19 days.

*Mutation prone.*—No.

*Disease resistance.*—Unknown.

*Temperature tolerance.*—Typical for carnation.

Foliage:

*Quantity.*—Numerous.

*Shape.*—Lanceolate.

*Texture.*—Smooth.

*Ribs.*—Central keeled.

*Arrangement.*—Bi-lateral along stem.

*Color.*—Upper side — Near to 141A.

*Size.*—Length: About 6 inches. Width: About ¾ to 1 inch.

*Stem.*—Color: Green.

Bud:

*Shape.*—Oval.

*Color.*—Near to 141C.
*Length.*—About 1⅓ to 1½ inches.
*Diameter.*—About ½ inch.

Calyx:
*Number of lobes (sepals).*—*About* 6.
*Length.*—About 1⅓ to 1½ inches.
*Width.*—About ½ inch.
*Color.*—Outside — Near to 141C. Inside — Near to 140D.

Bloom:
*Shape.*—Round.
*Size.*—Diameter average: About 3½ to 4 inches. Depth average: About 1½ inches.
*Borne.*—Terminal as standard.
*Color.*—General tonality: Hot pink. Upper side: Near to from 54A-D to 67C. Lower side: Near to from 54A-D to 68B. Center: Near to from 54A-D to 67C. Outer petals: Near to from 54A-D to 67C.
*Permanence.*—Yes.
*Keeping habit.*—18 to 21 days.
*Fragrance.*—None.

Petals:
*Number.*—About 52-54.
*Outer petals.*—Length: About 2½ inches. Width: About 1½ inches.

*Central Petals.*—Length: About 2½ inches. Width: About ¾ inches.
*Texture.*—Smooth.
*Form.*—Fan shaped, deeply serrated.
*Appearance.*—Shiny.

Reproductive organs:
*Stamen.*—Number: About 9 to 11. Arrangement: Around the ovary.
*Anthers.*—Number: About 9 to 11. Length: About ⅛ inch. Color: Near to 23D.
*Filaments.*—Length: About 1 inch. Color: Near to 19D.
*Pistil.*—Number: About 2. Length: About 1½ inches (mature). Color: Style — near to 50B fading to near white when mature.
*Stigma.*—Number: About 2. Color: Near to 150D fading to white when mature.
*Fetility.*—Male: Very poor. Female: Unknown.
*Ovary.*—Shape: Conical, ribbed. Color: Base — Greenish white. Body — Greenish yellow. Apex — Tan.

I claim:

1. A new and distinct variety of carnation plant, substantially as shown and described, characterized particularly by deeply serrated flowers of attractive deep pink coloration.

* * * * *

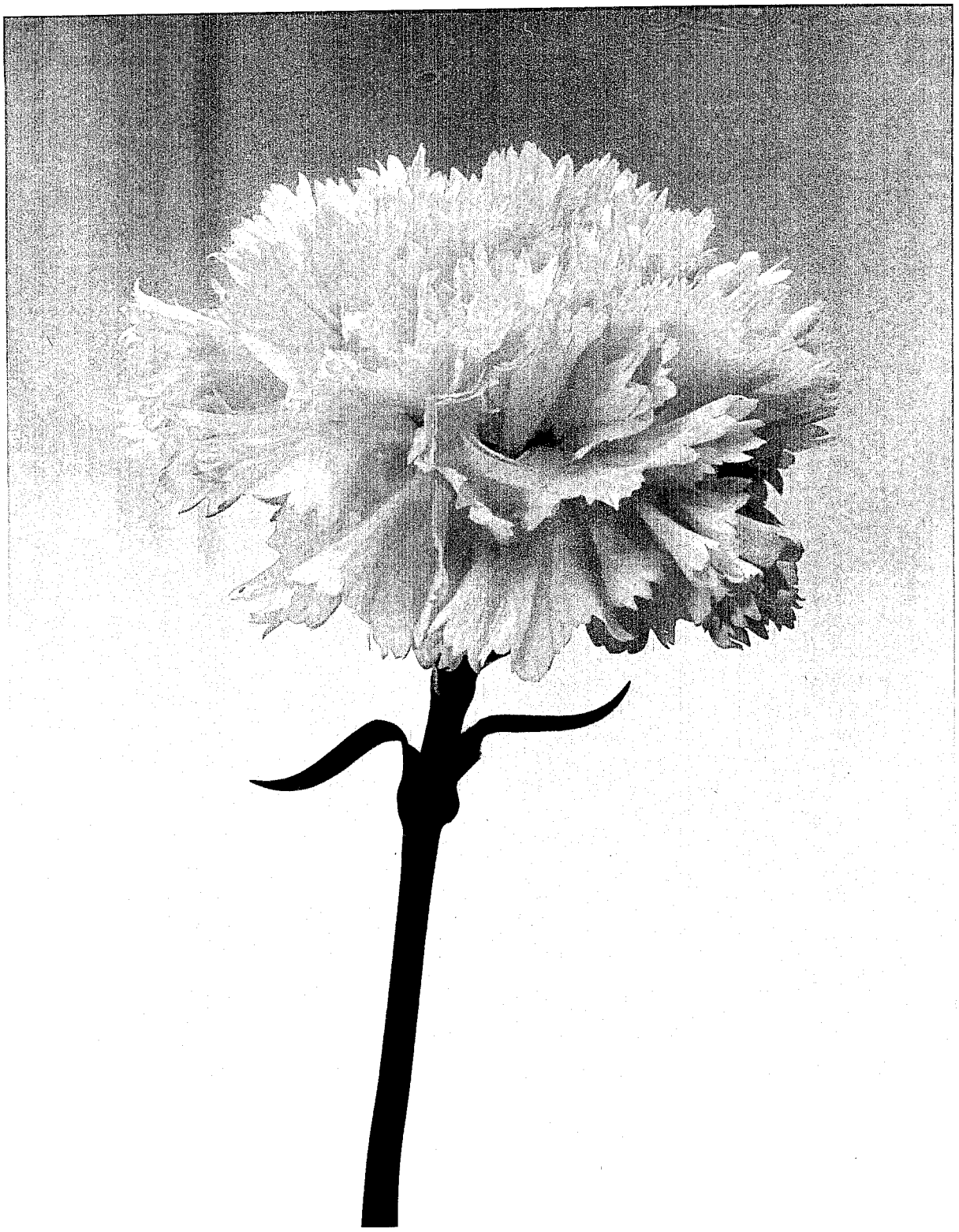

UNITED STATES PATENT AND TRADEMARK OFFICE

CERTIFICATE OF CORRECTION

PATENT NO. : Plant 7,859

DATED : April 28, 1992

INVENTOR(S) : Walter H. Jessel, Jr.

It is certified that error appears in the above-identified patent and that said Letters Patent is hereby corrected as shown below:

Column 1, line 33, after "shows" delete "a".
Column 1, lines 33,34, change "specimen" to -- specimens --.
Column 1, line 33, change "flower" to -- flowers --.

Column 2, line 2, change "espcially" to -- especially --.
Column 2, lines 42,43, between the lines beginning with "Color" and "Size" insert -- Underside - Near to 141B --.

Column 4, line 18, change "fetility" to -- fertility --.

Signed and Sealed this

Twenty-first Day of September, 1993

Bruce Lehman

*Attest:*

BRUCE LEHMAN

*Attesting Officer*

*Commissioner of Patents and Trademarks*